United States Patent
Johansson

(10) Patent No.: US 7,663,738 B2
(45) Date of Patent: Feb. 16, 2010

(54) METHOD FOR AUTOMATICALLY DETECTING FACTORS THAT DISTURB ANALYSIS BY A PHOTOMETER

(75) Inventor: Henrik Johansson, Espoo (FI)

(73) Assignee: Thermo Fisher Scientific Oy, Vantaa (FI)

( * ) Notice: Subject to any disclaimer, the term of this patent is extended or adjusted under 35 U.S.C. 154(b) by 342 days.

(21) Appl. No.: 11/665,021

(22) PCT Filed: Oct. 11, 2004

(86) PCT No.: PCT/FI2004/000603

§ 371 (c)(1),
(2), (4) Date: Apr. 10, 2007

(87) PCT Pub. No.: WO2006/040387

PCT Pub. Date: Dec. 20, 2006

(65) Prior Publication Data

US 2009/0009750 A1    Jan. 8, 2009

(51) Int. Cl.
*G01N 33/48*    (2006.01)

(52) U.S. Cl. .......................................... 356/39; 356/40

(58) Field of Classification Search ............. 356/39–42
See application file for complete search history.

(56) References Cited

U.S. PATENT DOCUMENTS

| 6,353,471 B1 | 3/2002 | Samsoondar et al. |
| 2002/0186363 A1 | 12/2002 | Samsoondar et al. |
| 2003/0202170 A1 | 10/2003 | Shepherd et al. |

FOREIGN PATENT DOCUMENTS

EP    1 059 522 A1    12/2000

OTHER PUBLICATIONS

Merrick Mark F. et al., Clinical Chemistry, vol. 32, No. 4, 1986, pp. 598-602.

*Primary Examiner*—Michael P Stafira
(74) *Attorney, Agent, or Firm*—Birch, Stewart, Kolasch & Birch, LLP

(57) ABSTRACT

The invention concerns a method for detecting the amounts of substances that may disturb chemical analysis performed by an analyzer for clinical chemistry. The presence and concentration of hemoglobin, bilirubin and lipemia are detected by measuring the absorbance or reflectance on at least two, preferably six, different wavelengths over the measured spectrum. The measurements are performed at two wavelengths for each substance, preferably on the absorbance peaks of the specific substance and on the root of the specific peaks. Since the three substances mentioned above each have at least one peak in the spectrum, the measurement is done on three peaks and three root positions respectively when three substances have to be measured.

7 Claims, 7 Drawing Sheets

| Lipemia | Measured | | | | Theoretical values | | |
|---|---|---|---|---|---|---|---|
| n. Calib data | Calib 2 | Calib 1 | Hemoglobin | Bilirubin | lipemia | hemoglobine | bilirubin |
| g/l | g/l | g/l | g/l | umol/l/100 | g/l | g/l | umol/l/100 |
| -0,75 | 0,08 | 0,21 | 4,91 | 4,93 | 0 | 5 | 5 |
| 5,95 | 4,64 | 4,94 | 0,31 | 5,45 | 5 | 0 | 5 |
| 1,59 | 1,47 | 1,07 | 1,93 | 1,93 | 1,65 | 1,65 | 1,65 |
| 1,09 | 1,16 | 0,82 | 0,19 | 5,28 | 1,25 | 0 | 5 |
| 5,83 | 4,54 | 4,80 | 0,36 | 1,66 | 5 | 0 | 1,25 |
| 1,04 | 1,13 | 0,79 | 0,21 | 1,49 | 1,25 | 0 | 1,25 |
| -0,77 | 0,07 | 0,21 | 4,92 | 0,41 | 0 | 5 | 0,5 |
| -0,80 | 0,06 | 0,20 | 2,39 | 2,40 | 0 | 2,5 | 2,5 |
| 5,81 | 4,53 | 4,77 | 0,34 | 1,64 | 5 | 0 | 1,25 |
| -0,21 | 0,39 | 0,34 | 3,30 | 3,31 | 0,33 | 3,33 | 3,33 |
| 3,88 | 3,05 | 2,74 | 0,69 | 0,70 | 3,33 | 0,33 | 0,33 |
| 6,01 | 4,69 | 5,02 | 0,84 | 0,34 | 5 | 0,5 | 0 |
| 1,09 | 1,16 | 0,82 | 1,52 | 0,23 | 1,2 | 1,25 | 0 |
| -0,77 | 0,07 | 0,21 | 1,21 | 4,87 | 0 | 1,25 | 5 |
| -0,75 | 0,08 | 0,21 | 4,81 | 0,41 | 0 | 5 | 0,5 |
| 0,02 | 0,52 | 0,40 | 4,92 | 0,09 | 0,5 | 5 | 0 |
| 1,63 | 1,50 | 1,10 | 0,62 | 1,89 | 1,65 | 0,33 | 1,65 |
| -0,32 | 0,32 | 0,31 | 0,32 | 0,33 | 0,33 | 0,33 | 0,33 |
| -0,22 | 0,38 | 0,33 | 0,30 | 0,24 | 0,33 | 0,33 | 0,33 |
| 5,47 | 4,25 | 4,37 | 0,29 | 0,62 | 5 | 0 | 0,5 |
| 0,54 | 0,83 | 0,58 | 0,91 | 0,83 | 0,83 | 0,83 | 0,83 |
| -0,66 | 0,13 | 0,23 | 0,31 | 4,58 | 0 | 0,5 | 5 |
| 1,11 | 1,17 | 0,83 | 5,07 | 0,17 | 1,25 | 5 | 0 |
| 1,75 | 1,58 | 1,16 | 1,85 | 1,73 | 1,66 | 1,66 | 1,66 |
| 2,77 | 2,26 | 1,83 | 0,33 | 0,32 | 2,5 | 0,5 | 0 |
| -0,63 | 0,15 | 0,24 | 5,33 | 5,24 | 0 | 6 | 6 |
| 7,14 | 5,63 | 6,51 | 5,88 | 6,17 | 6 | 6 | 6 |
| 8,23 | 6,58 | 8,14 | 0,33 | 8,30 | 7,5 | 0 | 7,5 |
| 9,70 | 7,95 | 10,63 | 10,31 | | 10 | 10 | 10 |
| -0,54 | 0,20 | 0,25 | 6,96 | 6,72 | 0 | 7,5 | 7,5 |
| 8,07 | 6,44 | 7,89 | 7,35 | 0,13 | 7,5 | 7,5 | 0 |
| -0,65 | 0,14 | 0,23 | 6,91 | -0,04 | 0 | 7,5 | 0 |
| 6,99 | 5,50 | 6,30 | 0,14 | 5,76 | 6 | 0 | 6 |
| 8,52 | 6,85 | 8,60 | 7,59 | | 7,5 | 7,5 | 7,5 |
| -0,60 | 0,17 | 0,24 | -0,03 | 9,01 | 0 | 0 | 10 |
| -0,58 | 0,18 | 0,25 | 9,47 | -0,02 | 0 | 10 | 0 |
| 9,63 | 7,88 | 10,50 | 0,38 | 0,20 | 10 | 0 | 0 |
| 8,10 | 6,47 | 7,94 | 0,24 | 0,08 | 7,5 | 0 | 0 |

Fig. 5

METHOD FOR AUTOMATICALLY DETECTING FACTORS THAT DISTURB ANALYSIS BY A PHOTOMETER

The present invention relates to a method for detecting the amounts of substances that may disturb chemical analysis performed by an analyzer for clinical chemistry.

BACKGROUND OF THE INVENTION

Samples of analyzers for clinical chemistry are usually serum or plasma that is separated from a blood sample by centrifugation. Some changes may occur in the sample during sampling, centrifugation and processing of the sample. These changes, for example hemolysis, alter the composition of the sample and compounds that may disturb the analysis of the sample may be generated. The serum or plasma sample may also contain higher than normal amounts of substances that disturb the measurement. Higher concentration of hemoglobin, bilirubine or lipemia may be caused by the medical condition of the patient. These components have strong colors or they are highly turbide. If these components are present in a concentration that is higher than normally, the analysis of the sample may be seriously disturbed and the analysis results distorted.

Faulty samples can be usually discovered visually because of anomalous color or turbidity. Of course, an accurate estimate of the concentration cannot be achieved by visual control. If several, disturbing components are present simultaneously, the valuation of the sample is even more complicated. By using visual control, only rejection of a faulty sample is possible. The defects in color of a sample can be detected only after centrifugation. Normally the samples have been checked before loading them to an analyzer. However, laboratory automation has made it possible to perform the centrifugation and feeding of the samples to the analyzers automatically. Therefore no visual control of the samples is used and faulty samples may enter the analyzer and cause wrong results. Since the results are often used in diagnosing diseases, it is extremely important to prevent any faulty results that may lead to wrong treatment or medication.

The main causes for disturbed analyze are hemoglobin, bilirubin and lipids. Additionally, medication that color the serum or plasma as well as biliverdine may cause difficulties in measurement. In analyzers that are presently on market, only three first mentioned substances are observed. The typical concentration of bilirubin is up to 500 µmol/l and values of 100-200 µmol/l are common, the highest values being 1000 mol/l. Lipeamia is present in amounts of 1-2 g/l, but even values of 10 g/l may exist. The amount of hemoglobin is in the range of 2-3 g/l, 5 g/l is consider to be rather high value and measuring range is usually limited to 10 g/l.

One way to measure bilirubin, hemolyse and lipemia is to use a diluted sample that is measured on three different wavelengths. The sample is diluted by water or saline and measured on wavelengths of 405, 425 and 700 nm. Measurement is done by direct absorbance measurement or via reflection. The sample is then classified in categories whereby a HIL-index is obtained. Every category corresponds with a certain concentration range. When a HIL-disturbance limit is exceeded an alarm is initiated. The wavelengths used may vary, but the handling of results is in basic similar in different apparatuses.

By studying the spectrum of a sample, it is clear that this method is reliable on samples that contain only one HIL-component. The spectrums of different components do overlap, whereby it is possible by this method to detect that something is wrong with the sample, but it is not possible to detect what are the components causing the problem or what are the concentrations of different components. If simple detection of a faulty sample is satisfactory, this method may well be used. If the concentration of every component is to be measured, the situation is more difficult. A raised concentration of lipemia raises the absorbance on all wavelengths whereby even bilirubin and hemoglobin obtain erroneous high values even though the concentration of these substance were on an acceptable level. Especially the interference of bilirubin and hemoglobin is difficult to control. Further weaknesses of this method is that it consumes some of the sample (5-10 µl) and adds measuring steps for each sample thereby reducing the analyzing speed and capacity of the analyzer.

An alternate way to detect HIL-components is to obtain an absorbance spectrum for the whole sample over wavelengths of 300-1000 nm. The sample may be diluted or undiluted and the measurement can be done directly by absorption or indirectly by reflection. The spectrum is detected either on a sample tube or in an intermediate storage (at the end of a pipette, for example). Various calculation algorithms may be used for studying the spectrum and reasonable good estimation of the concentration of different HIL-substances can be obtained. The benefit of this method is that no sample has to be wasted and the measurement does not spend the capacity of the analyzer. The method requires anyhow an extra spectrometer and transfer means for the sample. This raises the costs and the complexity of the apparatus considerably.

Abovementioned methods have been described in US 2002/0089669, U.S. Pat. No. 6,353,471, US 2001/0004256 and US 2002/0110487.

SUMMARY OF THE INVENTION

According to the present invention the presence and concentration of hemoglobin, bilirubin and lipemia are detected by measuring the absorbance or reflectance on at least two, preferably six, different wavelengths over the measured spectrum.

According to the other aspects of the present invention, the measurements are performed at two wavelengths for each substance, preferably on the absorbance peaks of the specific substance and on the root of the specific peaks. Since the three substances mentioned above each have at least one peak in the spectrum, the measurement is done on three peaks and three root positions respectively when three substances have to be measured.

Other objects and features of the invention will become apparent from the following detailed description considered in conjunction with the accompanying drawings. It is to be understood, however, that the drawings are intended solely for purposes of illustration and not as a definition of the limits of the invention, for which reference should be made to the appended claims.

Benefits of the Invention

The correlation between the measured results and theoretical concentration of known samples has been found to be good. In the preliminary test the correlation with the actual concentration of the test samples has been found to be close to the accuracy of a spectrometer. The invention can be implemented simply by changing the programming of the analyzer and no changes in the mechanical structure are necessary. No additional spektrophotometers or dosing means are needed. For this reason implementation of the invention is very cost effective and can be done even for existing apparatuses. Since

BRIEF DESCRIPTION OF THE DRAWINGS

FIG. 5 shows results of a test of a detection method performed according to the invention.

Figure 1:
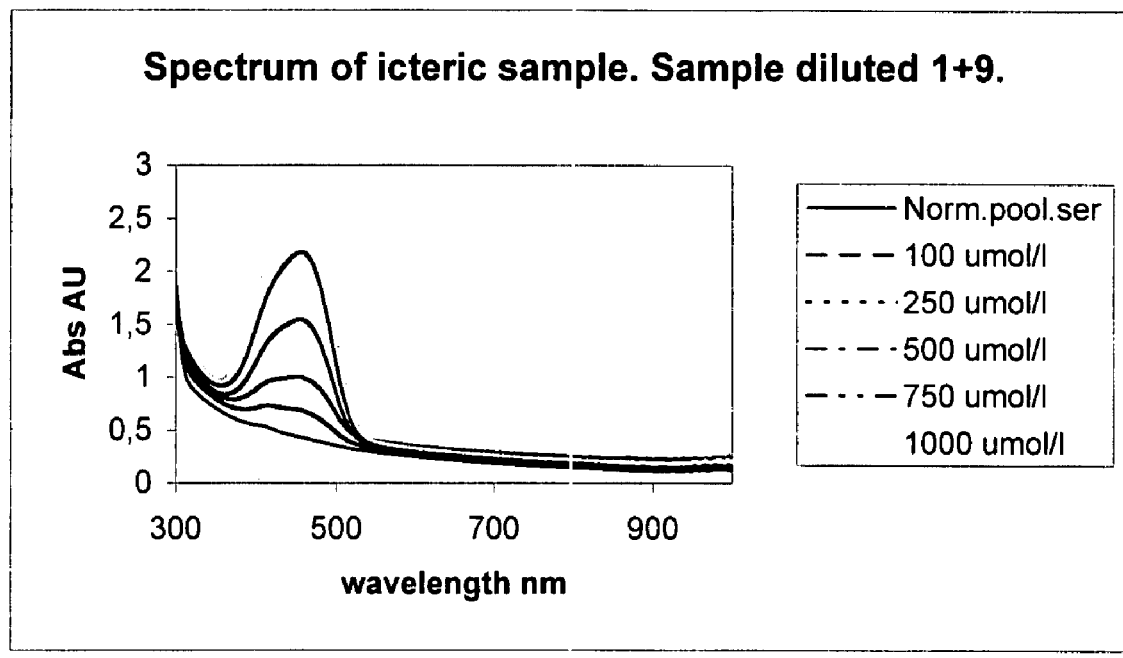
FIG. 1 shows a spectrum of a calibration samples for bilirubin.
Figure 2:
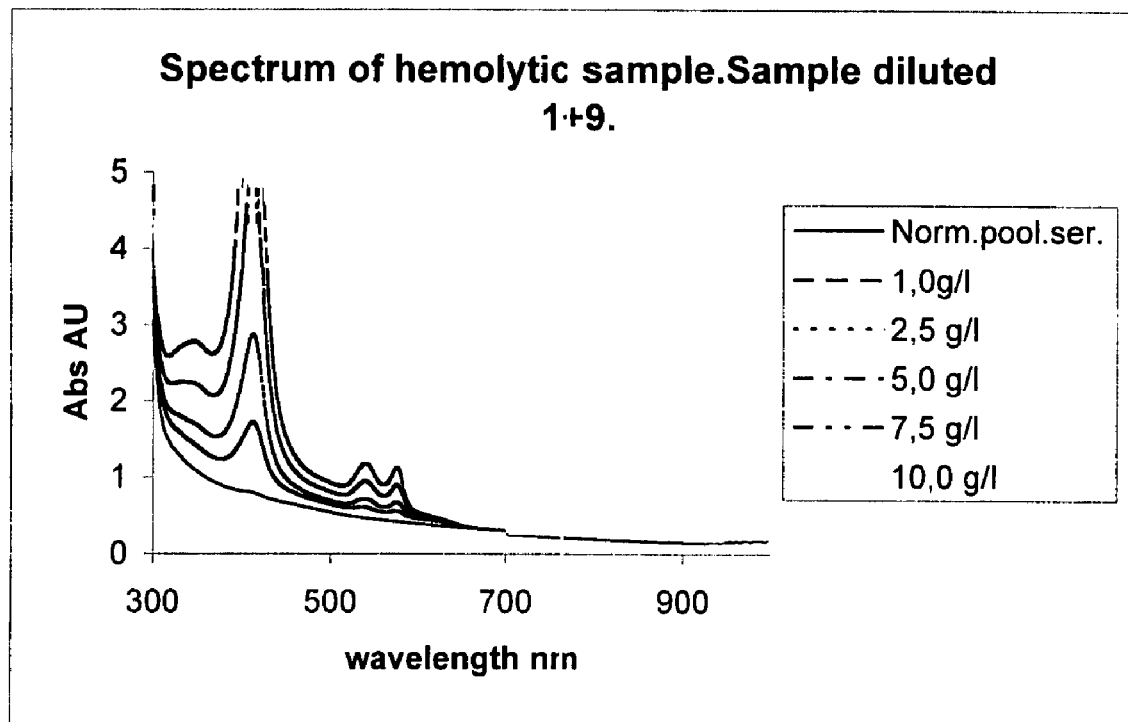
FIG. 2 shows a spectrum of a calibration samples for hemoglobin.
Figure 3:
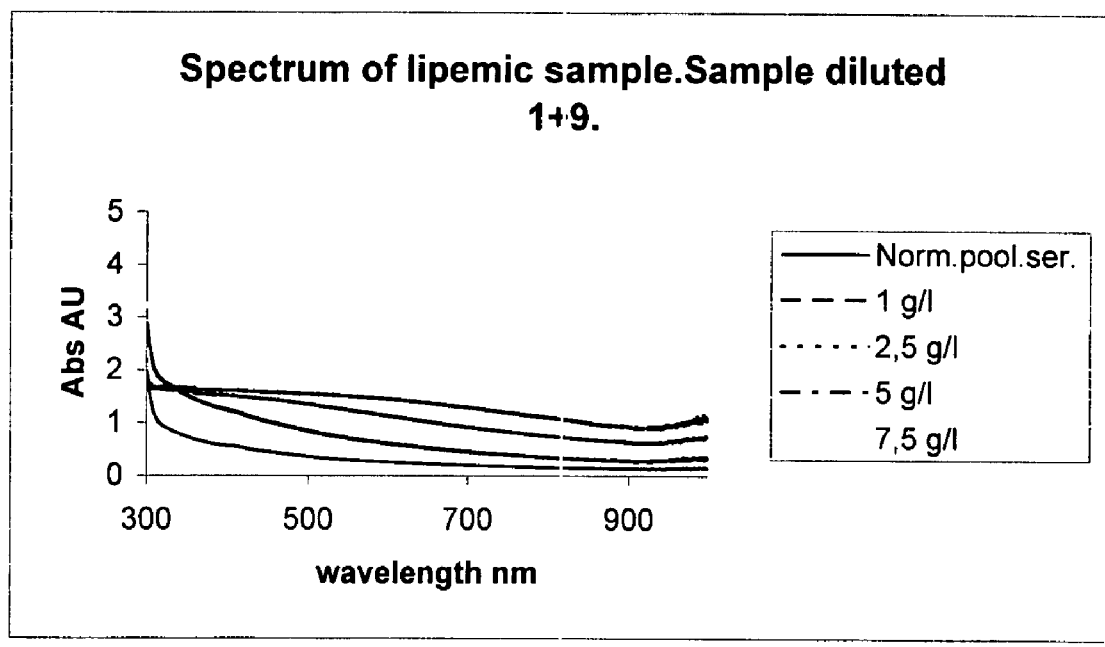
FIG. 3 shows a spectrum of a calibration samples for lipemia.

The charts in FIGS. 1-3 were measured by a Shimadzu spectrophotometer. The samples were made by adding hemoglobin, bilirubin and lipemia into samples of a patient pool having normal concentration levels. Before the measurement of the spectrum, samples were diluted in relation of 1 to 9 by a solution of a 0.9% NaCl.

Bilirubine disturbs the measurement and detection by its own very high light absorption by raising the level of absorption. A sample having 500 μmol/l of bilirubin gives even when diluted by 1 to 10 an absorbance level of 1.6 A on a wavelength of 410 nm. Absorbance peak is relatively wide. The effect thereof starts from about 500 nm and reaches to the area of UV wavelengths. Tests having an absorption measurement on this area are disturbed. Further, bilirubin may decompose during the proper reaction of the test and thereby affect or be part in the measurement of the kinetic reaction speed. Bilirubin can also affect through its decomposition products.

Lipemia blurs the sample and scatters light. The result is a raise in absorbance level. The chance in level is higher the shorter the wavelength of the light is. The effect spreads over the whole range of visible light and far further. The change in absorbance is strong, 5 g/l (intralipid) diluted by 1 to 10 gives an absorbance level of about 0.7 A on wavelength of 800 nm and on 400 nm the same solution gives a level of about 2.7 A. Lipemia disturbs measurement on all wavelengths.

Hemoglobin disturbs the measurement by its own absorption. Hemoglobin has three rather sharp absorption peaks on wavelengths of 405, 540 and 575 nm. Tests that are performed on the range of these peaks are badly disturbed. Especially on 405 nm the absorption is high. A sample having 5 g/l hemoglobin gives when diluted by 1 to 10 an absorption of 2.5 A on wavelength of 405 nm.

Figure 4:
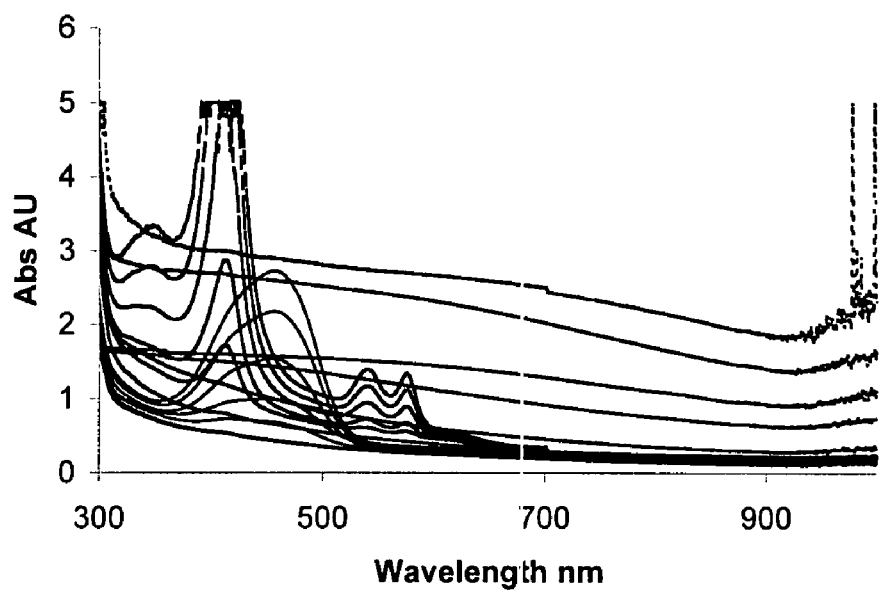
FIG. 4 shows the abovementioned spectrums in a same chart.

When above mentioned HIL-components present simultaneously in a single sample, which often is possible, the detection of the components is remarkably difficult. FIG. 4 shows that on wavelengths near 400 nm all substances have a peak that overlaps the peaks of both other substances. From FIG. 4 it can be seen that it is impossible to find a wavelength for bilirubin and hemoglobin measurements on which the other substance would not be present and interfering. Lipemia is the only substance that can be measured without interference with the other two components, but it interferes itself with these two components.

DETAILED DESCRIPTION OF THE PRESENTLY PREFERRED EMBODIMENTS

The idea of the invention is to use several different wavelengths of light for measuring the absorbance (or reflectance, when applicable) of a sample in order to sort out the concentrations of at least two, preferably three substances that disturb the analysis of a sample. The invention is intended to be used in an analyzer that examines the samples by directing a beam of light on a sample. The absorbance of the sample is then measured either directly or indirectly through reflectance. Normally the analyzer is capable of measuring at different wavelengths for different type of analyses. According to the invention the absorbance of a sample is preferably measured on a wavelength on which a peak in absorbance exist for a specific substance. Additionally, the absorbance is measured on a wavelength that differs from the initial wavelength. The second measurement is performed preferably on a wavelength that is in the vicinity of the root of the peak in question. For three substances mentioned above, six measurements are needed, one for each peak and one for each root. This method indicates if the measured peak for a substance really exists or whether the absorbance is higher than normal of other reasons. In this case the reason being the presence of other two substances that are measured herein. This indication gives essentially the same information as a derivative of the spectrum, i.e. the increase in absorbance caused by the interfering substance in question would be indicated regardless of the basic level of the absorbance in the sample in question. This means that by measuring absorbance on six different wavelengths presence and amount of all HIL-interferents could be detected. No additional photometers or dosing means are needed. The HIL-detection can be one additional dosing wherein the sample is diluted and measured on six wavelengths, for example. By using correction algorithms, the concentrations of HIL-components can be calculated independently from each other. The number of measurements is dependent of the number of substances to be detected. If only two substances are present, four measurements are needed. If it is known that only one interfering substance is present, the absorbance thereof can be measured directly by one measurement on the peak value and the use of the invention is not necessary.

The off-peak measurement can be done on either side of the peak, but since the absorbance values of all HIL-components generally decrease towards the longer wavelengths, it may be beneficial to locate the off-peak measurement on a longer wavelength than the measurement on the peak.

Test Results

In order to verify the applicability and reliability of the invention, a number of measurements were made by a Konelab 30 analyzer. This analyzer is a standard apparatus used for clinical analysis. The samples were a patient pool having normal concentration levels and the same pool wherein different amounts of HIL-compounds were added.

Parameters:

All samples and calibrators were defined on a dosage wherein 10 μl of sample were diluted with 90 μl of 0.9% NaCl solution.

The measurements were performed on two wavelengths for each component in a following way:
Hemoglobin 575 nm and 600 nm
Bilirubine 450 nm and 510 nm
Lipemia 660 nm and 880 nm As can be seen on FIGS. 1-4, these wavelengths do not locate accurately on peaks and roots of the spectrum of each substance. The reason to this is that the measurements had to be limited to wavelengths readily available in Konelab 30 analyzer. Different choice of wavelengths might give improved results.

Calculation of Results

In calculating the results the following calibration and interference equations were used.

Concentration of lipemia is calculated directly from a calibration equation.

$$\text{Lip conc. (g/l)} = K*(\text{lip.resp})*(\text{lip.resp}) + L*(\text{lip.resp}) + M$$

Wherein lip.resp is the measured response of the analyzer.

Hemoglobin value is corrected in relation to lipemia with an equation:

$$(\text{resp.lip/hem}) = -N*(\text{lip.conc g/l})*(\text{lip.conc g/l}) + O*(\text{lip.kons g/l}) + P$$

This response is deducted from hemoglobin response:

$$\text{Hemresp(corr.)} = \text{hemresp(tot)} - (\text{resp.lip/hem})$$

The consentration is calculated by equation:

$$\text{Hem.conc. (g/l)} = Q*\text{hemresp(corr.)} - R$$

Bilirubin concentration is obtained from equation:

$$\text{Bil.conc. (umol/l)} = (S*\text{bilresp(corr.)} - T)*U$$

Factors K-U are constants.

Figure 6:
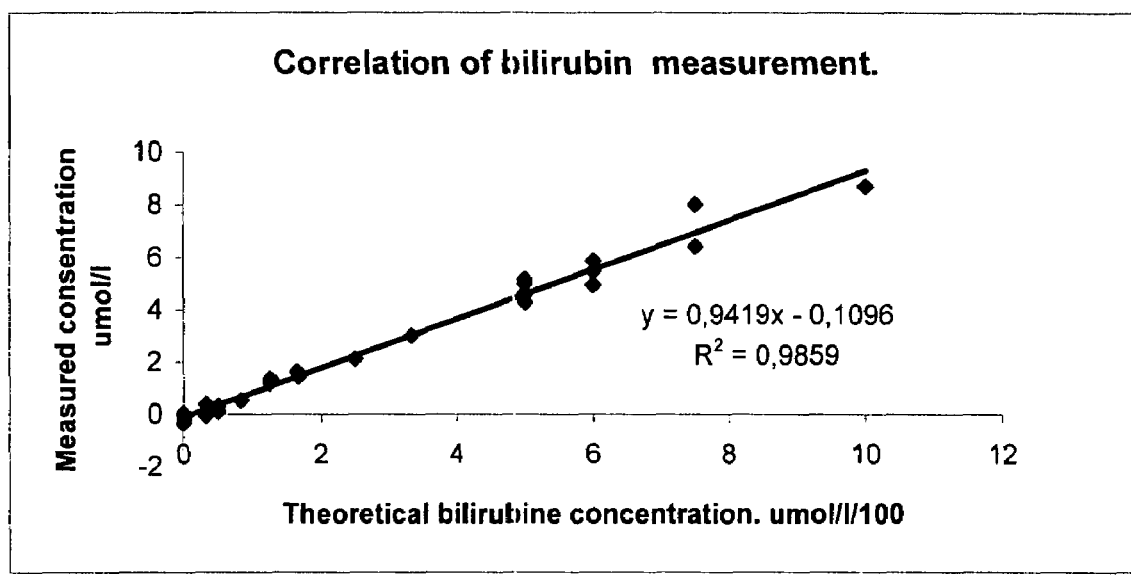
FIG. 6 shows the correlation between detected values of bilirubin and theoretical concentration.
Figure 7:
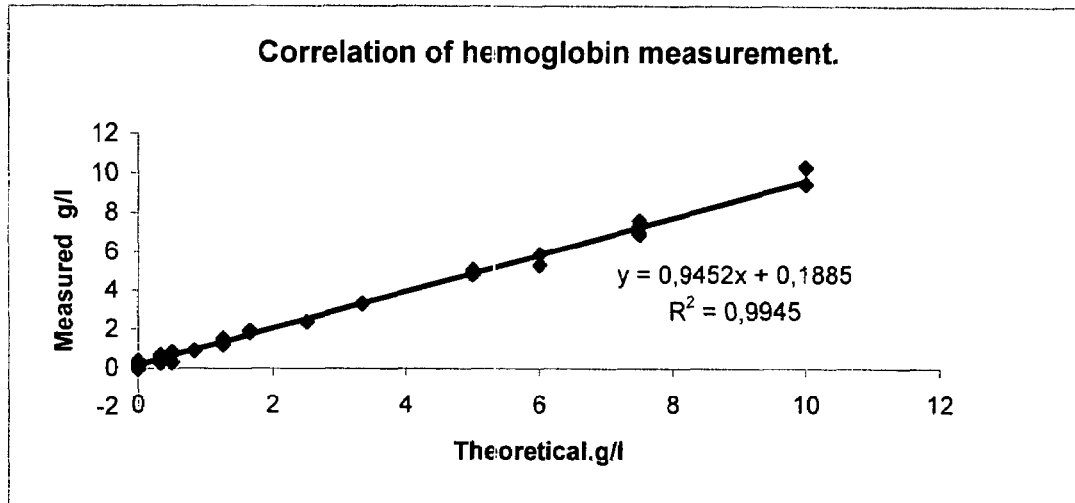
FIG. 7 shows the correlation between detected values of hemoglobin and theoretical concentration.
Figure 8:
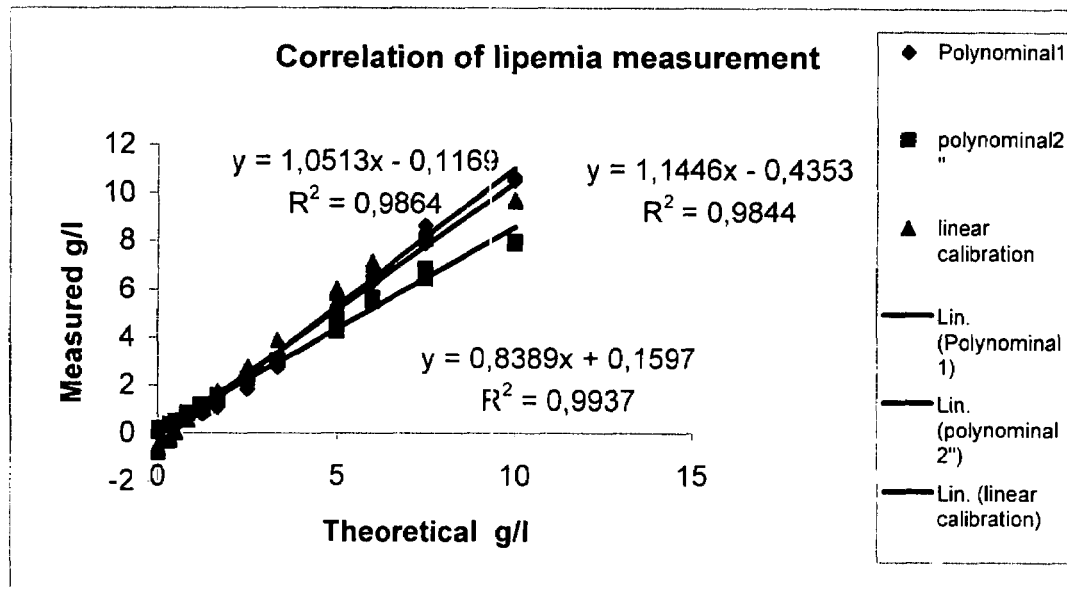
FIG. 8 shows the correlation between detected values of lipemia and theoretical concentration.

The operability of the calculation were tested on trial measurements wherein 38 samples made from normal pool by adding lipemia, bilirubin and hemoglobin were analyzed. Lipids were calculated by three different calibrations, by two different polynome-based calibration curves and by one linear fitting. The results are shown in FIG. 5 in a table and the correlations are shown in FIGS. 6-8. The correlation was surprisingly good and seems to be reliable enough for classifying the samples in groups according to concentrations of interfering or disturbing substances.

One other notable feature is that the invention seems to be operable even if the measurements are not preformed on wavelengths of peaks in spectrum and on the roots of the peaks.

Thus, while there have been shown and described and pointed out fundamental novel features of the invention as applied to a preferred embodiment thereof, it will be understood that various omissions and substitutions and changes in the form and details of the method may be made by those skilled in the art without departing from the spirit of the invention. For example, it is expressly intended that all combinations of those method steps that perform substantially the same results are within the scope of the invention. Substitutions of the elements from one described embodiment to another are also fully intended and contemplated. It is also to be understood that the drawings are not necessarily drawn to scale but they are merely conceptual in nature. It is the intention, therefore, to be limited only as indicated by the scope of the claims appended hereto.

What is claimed is:

1. Method for detecting in a sample the presence and concentration of at least two substances selected from a group consisting of hemoglobin, bilirubin and lipemia, wherein the method comprises:
    measuring the absorbance or reflectance of light directed on a sample using at least two different wavelengths for measuring the absorbance or reflectance of any one of the substances selected from the group consisting of hemoglobin, bilirubin and lipemia, and being present in the sample;
    performing at least one measurement on a wavelength that is on an absorbance peak of one substance; and
    performing at least one second measurement on a root area of an absorbance peak of the substance of which one measurement is performed on a wavelength that is on the absorbance peak of the substance.

2. Method according to claim 1, wherein all members of the group consisting of hemoglobin, bilirubin and lipemia are present in the sample and six different wavelengths are used for measuring the absorbance or reflectance of the substances.

3. Method according to the claim 1, wherein for each substance measured, one measurement is made at the wavelength of the absorbance peak and one at the root area of the absorbance peak.

4. Method according to claim 1, wherein at least one second measurement is performed on a wavelength that is greater than the wavelength of the first measurement for the same substance.

5. Method according to the claim 2, wherein for each substance measured, one measurement is made at the wavelength of the absorbance peak and one at the root area of the absorbance peak.

6. Method according to claim 2, wherein at least one second measurement is performed on a wavelength that is greater than the wavelength of the first measurement for the same substance.

7. Method according to claim 3, wherein at least one second measurement is performed on a wavelength that is greater than the wavelength of the first measurement for the same substance.

* * * * *